United States Patent [19]

Fleisher et al.

[11] Patent Number: 5,441,612
[45] Date of Patent: Aug. 15, 1995

[54] RADIATION-ENHANCED RECOVERY OF MALTOL

[75] Inventors: Alexander Fleisher, Wayne; Ian Gorenstein, Edgewater; Olga Vselyubskaya, Leonia; Ilya Nakhimovich, Bloomfield, all of N.J.

[73] Assignee: Florasynth, Inc., Teterboro, N.J.

[21] Appl. No.: 268,649

[22] Filed: Jun. 30, 1994

[51] Int. Cl.⁶ ............................................. C07C 7/00
[52] U.S. Cl. .................. 204/157.15; 204/157.6; 204/157.63; 204/157.69; 204/157.9; 204/157.93
[58] Field of Search ............ 204/157.15, 157.6, 157.63, 204/157.69, 157.9, 157.93

[56] References Cited

U.S. PATENT DOCUMENTS

| | | | |
|---|---|---|---|
| 2,457,203 | 12/1948 | Brasch | 204/157.63 |
| 3,034,974 | 5/1962 | Lowry | 204/157.63 |
| 3,326,786 | 6/1967 | Kinoshita et al. | 204/157.9 |
| 3,522,091 | 7/1970 | Lapidot | 204/157.15 |
| 3,801,432 | 4/1974 | Free | 204/157.69 |

OTHER PUBLICATIONS

CA 80: 79684 "Effect of gamma radiation on the production of aroma components in apples during ripening and storage."

*Primary Examiner*—John Niebling
*Assistant Examiner*—C. Delacroix-Muirheid
*Attorney, Agent, or Firm*—Scully, Scott, Murphy & Presser

[57] ABSTRACT

The yield and recovery of desirable aromatic principles such as maltol, from source material and especially from plant material, are improved by irradiating the source material with gamma radiation and then extracting from the irradiated material a product comprising the desired principle.

16 Claims, 2 Drawing Sheets

RADIATION-ENHANCED RECOVERY OF MALTOL

BACKGROUND OF THE INVENTION

The present invention generally relates to the recovery of desirable, useful aromatic, that is, odoriferous principles from source material. More specifically, it relates to recovery of product fractions, such as oleoresins, containing the desired aromatic principle from source material such as plant material in which such aromatic principles occur naturally. The term "aromatic" as used herein is intended to refer to the aroma-possessing property of the material; the term is not intended to be confined to the chemical context of possessing an "aromatic" ring structure.

In particular, this invention relates to the recovery of aromatic resin from foliage of coniferous evergreens which contain substantial quantities of maltol (2-methyl-3-hydroxy-4-pyrone). Maltol is a heterocyclic aromatic chemical used extensively in flavor and fragrance compositions. The resin obtained by the process described in the present invention can be used as an ingredient in flavor or fragrance compositions or as a commercial source for the recovery of natural maltol. The invention relates more generally to the improved recovery of maltol and other aromatic principles from other source material, such as resin or other products representing a relatively concentrated form of the desired active relative to its content in native plant material.

The recovery of desirable aromatic principles from plant material generally involves as one step the treatment of all or part of the plant material to recover a resin, oleoresin, or other concentrate, and then treatment of that product to recover the desired aromatic principle in further concentrated or even pure form. The oleoresins recoverable from the coniferous trees are well known in the flavor, fragrance, cosmetic and pharmaceutical industries. The resin extracted from balsam fir (*Abias balsamea* L.) is the most widely known, and is even allowed to be used in food.

Hundreds of botanical species are used as raw materials and in each case a particular part of the plant such as leaves, stems, bark, fruit or flowers are found to be most suitable. Despite the variety of plant sources and the multitude of solvents that can be used in the extraction process, all known methods have one common basis. This is a preferential solubility and affinity of the aroma determining substances for the chosen solvent. The process of extraction is, in fact, preferable diffusion of aroma carrying chemicals from the plant material into a solvent phase. The chemicals can be concentrated and recovered from the solvent phase by stripping, usually through a distillation process.

Numerous extraction means used for contacting plant material with the solvent are designed to speed up and intensify the diffusion process. Despite the multitude of botanical sources and known extraction techniques, they can be divided into two major groups—those which use dehydrated plant material and those in which the oleoresin is extracted from fresh plant tissues. Cinnamon bark, black pepper, various fruits of the Umbelliferae family such as cumin, caraway, celery, etc. can be used as examples of plant material which is extracted dry. Rose flowers, jasmine, tuberose and lavender are examples of plant material which is extracted fresh.

Hardy raw materials which are mentioned in the first group usually retain their aromatic values through the dehydration process, while gentle tissues of flowers generally completely surrender their aromatic principals. The dehydration process alters the cell structure of the plant tissue, creating pores and cavities accessible to solvents and thus making the diffusion process reasonably quick. The plant material extracted fresh usually consists of flowers with gentle and thin petals which, despite the presence of water, offers low resistance to the diffusion.

The difficulty in conducting the extraction process becomes rather severe when hardy plant material is to be extracted but some or all of the aromatic values do not survive dehydration. Such is the case of a variety of coniferous plants and, in particular, various species of fir. The needles of the fir trees are specifically adapted to a very low rate of water evaporation therefrom and offer hard resistance to the penetration of the solvent. Thus, simple contact of fir needles with solvents results in very slow extraction. Due to the specific shape of the needles, a rough grinding is not efficient either, since breaking of the needle exposes only a small cross section to solvent penetration. It is, of course, possible to grind or to disperse fir needles into very fine particles. Such a process, however, is very expensive and for many reasons impractical.

The presence of maltol in the coniferous trees in general, and in the balsam fir (Abias spp.) specifically, is well established in scientific literature. Maltol has also been reported to be in the bark of some species of larch (Larix spp.) trees. Maltol is present in larch bark in combined form to an extent varying from about 0.1 percent to about 2 percent by weight depending upon the bark layer and the season of harvest. The richest supply of maltol is found in the bark of roots of the larch trees although, for practical reasons, not much root bark is harvested. Large quantities of larch trees and bark containing maltol exist and are available primarily in the northwest part of the United States and southwest Canada,. The bark is available at sawmills where it is stripped off of larch trees and stored in a pile, there to be burned for fuel or otherwise used if economical processes for recovering useful components therefrom can be found.

Limited quantities of fir balsam oleoresin are steadily produced by the extraction of dehydrated fir needles. The yield of oleoresin is rather low and so is the maltol content in it. The product is, therefore, costly and usually is employed only in expensive flavor and fragrance compositions. Due to its high cost and the low content of maltol, fir balsam oleoresin has not been seriously considered to be a practical source for recovery of maltol. Indeed, dehydration of the fir needles causes loss of essential oils, reduction in the yield of oleoresin, and a severe decrease in the maltol content of the product which is thereafter recovered.

Despite the attractiveness of maltol and of oleoresins containing maltol, recovering significant amounts of maltol using known extraction techniques has proven to be difficult or disappointing.

Maltol is insoluble in non-polar hydrocarbons, which renders solvent extraction with such solvents unsuitable for recovering maltol-containing resin from plant material. Although maltol is soluble in hot water, the data in scientific and patent literature indicates that maltol cannot be efficiently recovered from plant material by hot water extraction.

Maltol shows substantial solubility in polar solvents such as acetone, alcohol, and the like. However, these solvents are water soluble and will dissolve not only maltol but also all the eater contained in the fresh plant source material. This property makes subsequent recovery of the oleoresin or the maltol a difficult task. Utilization of water immiscible solvents (in which maltol is still soluble) for the extraction of fresh plant material by conventional techniques is restricted by the presence of water as described above.

In the course of development work aimed at the recovery of maltol from the foliage of coniferous species and, in particular, balsam fir, several drawbacks have been observed.

Oleoresin with high maltol content can only be recovered from fresh fir plant material. Dehydration (whether induced artificially or naturally) of the plant material results in a very substantial decrease of recoverable maltol to the point that the resin extracted from dry needles becomes an unsuitable source for practical recovery of maltol. This creates the necessity to work with fresh needles in the attempt to extract resin with a high maltol content, but leads to further drawbacks.

It has repeatedly been shown that treatment of fresh needles with hot water or steam results in a substantial decrease of recoverable maltol. Although the metabolic cycle of maltol is not clearly known, it may be concluded from scientific literature that maltol undergoes rapid changes in the plant tissue which may be effected by the conditions under which the recovery process is conducted.

The handling of large quantities of fresh plant material presents a serious problem because of the tendency of the plant material to heat up and ferment quickly in a densely pressed form.

In addition, the present inventors have found that woody branches of firs contain practically no maltol and represent undesirable ballast in the extraction process. The presence of thick woody parts soaked with solvent makes the environmentally required cleaning of spent material much more difficult. On the contrary, pure needles can be stripped of the solvent in approximately one-third of the time it takes to clean the mixture of needles and woody parts. However, stripping needles from the branches by physical or mechanical means prior to extracting a maltol-bearing product from the needles is an unacceptably time consuming step.

Thus, there still remains a need for a method for recovering a product fraction comprising a desired aromatic principle, and particularly maltol-containing oleoresin, from a source such as plant material.

It is an object of the present invention to improve the recovery of oleoresins from source material including fresh plant material.

It is another object of the present invention to reduce or eliminate the deleterious effect of plant material dehydration on the maltol content. It is thus a further object of the present invention to increase the recoverable maltol content of plant material.

Another object of the Present invention is to enable aromatic principles such as maltol to be recovered from source material more readily using materials (including solvents) which pose a lessened risk, or no risk, of hazard to personnel handling them and to the environment.

Yet another object of the present invention is to facilitate the separation of fresh needles from the woody branches of coniferous species.

A further object of the present invention is to reduce or eliminate the tendency of stored fresh plant material to undergo spontaneous heating and/or fermentation and/or composting when such a tendency is not desired.

BRIEF SUMMARY OF THE INVENTION

In one aspect, the present invention is a process for recovering an aromatic principle from source material containing it, comprising irradiating said source material with gamma radiation, and then extracting a fraction comprising said aromatic principle from said irradiated source material.

Another aspect of the invention comprises a process for recovering oleoresin, particularly maltol-bearing oleoresin, from plant material in the form of branch material having needles extending therefrom, comprising irradiating said branch material and needles with gamma radiation under conditions effective to weaken the attachment of the needles to said branch material, preferably to the point that at least some of the needles fall off the branch material, and then recovering the desired product fractions from the needles.

Another aspect of the present invention is the process which comprises irradiating branch material, having needles attached thereto, with an amount of gamma radiation effective to weaken the attachment of the needles to the branch material, and thereafter recovering said needles separate from the branch material.

DETAILED DESCRIPTION OF THE INVENTION

Figure 1:
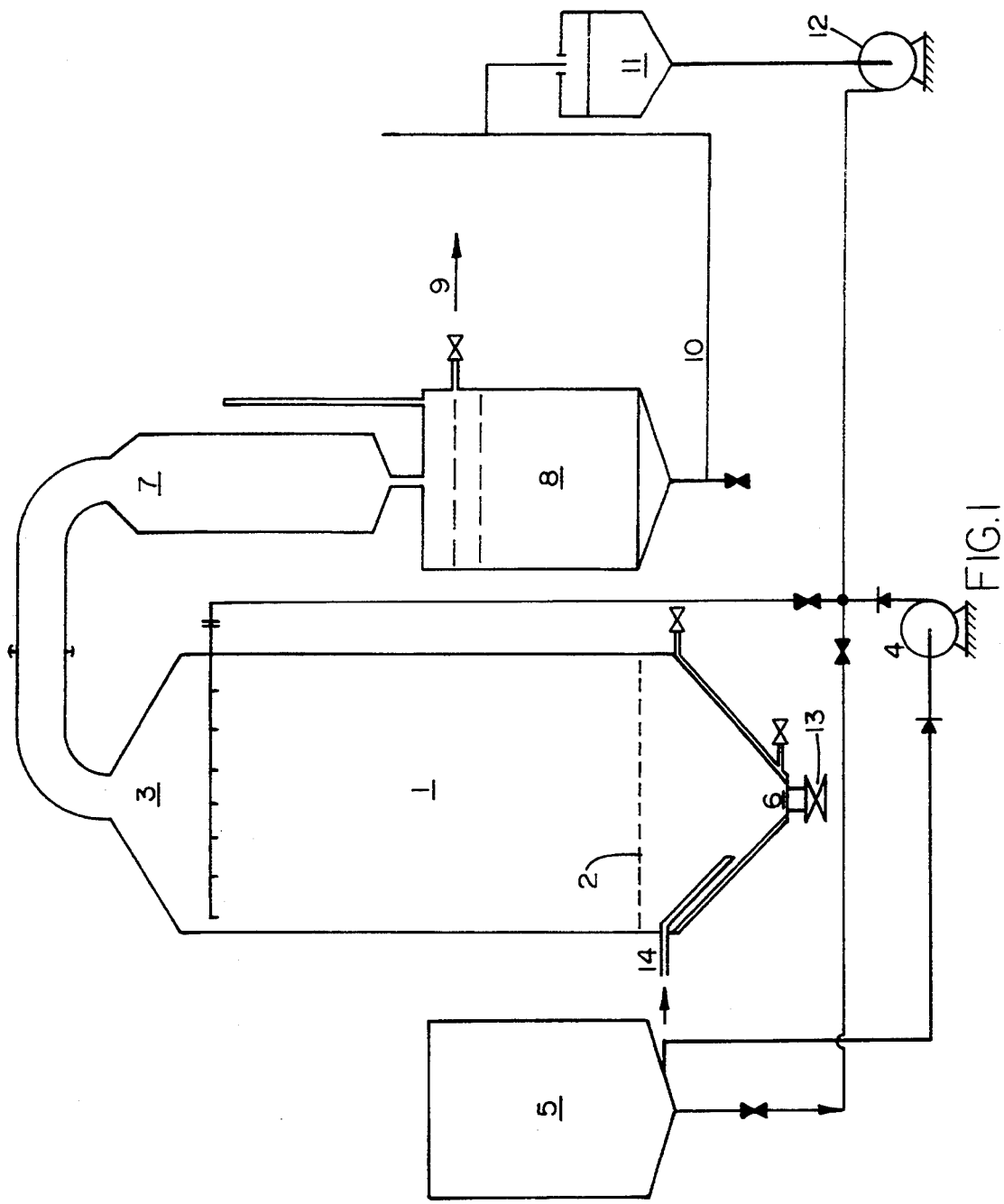
FIG. 1 is a flow chart of a preferred apparatus for recovering a product containing aromatic principle from material treated by the method of the present invention.

The present invention is useful for treating source material that is water-free, but is preferably used to treat source material that is hydrous, by which is meant source material that contains water. The source material can, of course, be solid, yet hydrous; a preferred example of such source material is fresh (that is, not totally dehydrated) plant materials such as needles, leaves, bark, branches and other plant tissue. A particularly preferred hydrous source material is fir foliage, in particular balsam fir foliage, including branch material (by which is meant limbs, smaller branches, and twigs, having needles extending from all or part thereof). Another preferred source is larch foliage or bark. The moisture content of hydrous source material treated in accordance with the method of the present invention can range from on the order of 1 wt. % up to 10 wt % and even higher, that is, up to 50 wt. % moisture content or higher.

The method of the present invention is useful in recovering oleoresin from such source material. The oleoresin is generally comprised of one or more organic aromatic principles, a particularly preferred example of which is maltol. The "oleoresin" which is removed from source material by the method of the present invention may comprise all resinous components present or a desired fraction thereof.

It is also possible to use the method of the present invention to treat oleoresin or other "concentrates", that is, products in which the maltol or other desired aromatic principle has been obtained from natural plant material (whether the concentration of the desired active is greater than, less than, or the same as its concentrations in the natural plant source).

In practice, the source material is exposed to gamma radiation. For recovering an aromatic principle, the gamma radiation intensity and the duration of exposure thereto are selected so as to increase the recovery of the aromatic principle in subsequent extraction processing, compared to the recovery without the irradiation. For treating branch material to facilitate subsequent treatment of the needles extending therefrom, the gamma radiation intensity and duration are selected to loosen the attachment of the needles to the branch material. Gamma radiation is generally defined as radiation in the range of $10^4$ to $10^7$ electron volts (eV), that is $1.6 \times 10^{-8}$ to $1.6 \times 10^{-5}$ ergs. More preferably, the gamma radiation to which the material is exposed for the purposes disclosed herein amounts to an energy level of about 0.5 to about 2.5 MRAD or higher.

Following the irradiation, the irradiated material can be treated by any means effective to extract the desired aromatic principle from the irradiated material. If the desired aromatic principle is water-soluble, extraction can be carried out with water; with an aqueous solution of salt (especially an alkali or alkaline earth metal halide, phosphate or sulfate), or a nonionic solute; with a non-aqueous polar solvent such as an alkanol, ketone, or glycol containing 1 to 8 carbon atoms (such as methanol, ethanol, propanol, isopropanol, any butanol, acetone, methyl ethyl ketone, ethylene glycol, or propylene glycol); with a solution in water of any such alkanol, ketone, or glycol; or with a mixture of water and a water-immiscible solvent such as 1,1,1-trichloroethane or trichloroethylene; or by other solvent for the desired aromatic principle.

The present invention thus facilitates extraction without having to use solvents that could be harmful to personnel using them or to the environment. Thus, the present invention is notably useful compared to prior extraction techniques.

This extraction is carried out using techniques conventional and readily apparent to the skilled practitioner, generally involving affording a high degree of contact between source material surfaces and the extractant.

It is not necessary to subdivide the source material to any particularly fine particle size, although it will be recognized that, depending on the form of the source material, some reduction in size may be appropriate if an improvement in the extracting and stripping efficiency or yield can be afforded without encountering increased difficulties in material handling.

Temperatures and contact times should also be chosen to afford the desired extraction yield and recovery.

The product stream recovered from the extraction comprises a useful source of the desired aromatic principle, e.g., maltol or otherwise. The extractant can be evaporated away, leaving a concentrated oleoresin fraction which can be used as such in the formulation of products such as, for example, personal care cosmetic products. However, this product stream can also be treated as is, or following further concentration or even complete removal of the extractant, to recover any particularly desired component fraction or compound, such as maltol.

For the recovery of maltol, following partial concentration of the extractant solution (to e.g. about 30% solvent), the concentrated extract can then be sequentially extracted with three portions of hot water at a 2:1 volume ratio (water:extract). The liquid phases separate easily on standing, whereupon the aqueous phases which contain maltol are combined and filtered, and the maltol can be recovered by extraction with methylene chloride using e.g. the "Poroplast" method described in A. Fleisher, "The Poroplast Extraction Technique in the Flavor and Fragrance Industry," *Perfumes and Flavorist* 15(5): 27-36 (1990). The solvent is stripped to provide crude maltol which can be recrystallized from 90% aqueous methanol which contains a small amount of EDTA.

FIG. 1 shows an apparatus that can be used in extracting the desired oleoresin fraction from irradiated plant material. Tank 1 is an enclosed vessel having a perforated plate 2 near its lower end and an exit passageway 3 at its top.

Plant material is loaded into tank 1 onto perforated plate 2. A sufficient amount of extractant (e.g., 1,1,1-trichloroethane or trichloroethylene) is pumped by pump 4 from a reservoir 5 and accumulates in the bottom 6 of the tank where it is evaporated by heating means (such as a heating coil). The rising vapors of the extractant contact the plant material. A portion of the extractant carries water vapor out through passageway 3 as a vapor stream. Substantial quantities of extractant also condense on the surface of the plant material providing a thin layer of the extractant.

The vapor stream leaving through passageway 3 passes into condenser 7 wherein it forms a liquid condensate which falls into separator 8 from which the water phase is removed as stream 9 for purification and discharge. The condensed extractant is removed as stream 10 into receiver 11 from which it is periodically pumped by pump 12 to the top of tank 1 where it washes down the extract which is formed on the surface of the plant material.

When the extraction is completed (as can be determined experimentally, for instance, by the reduction of the moisture content of the source material or by the oleoresin content of the solution), the concentrated resin solution in the extractant is discharged from area 6 of the tank through valve 13 for further purification. Residual extractant retained by the plant material can be removed by passing water steam 14 into the tank so as to pass through the plant material. Steam passing through the plant material removes the extractant with water. The extractant and water phases go through the condenser, separator and receiver. However, in this case the extractant is not returned to the extraction tank but is pumped into the pure fresh extractant reservoir 5.

It will also be recognized that the present invention also provides a useful technique for facilitating the recovery of needles from any species of needle-bearing evergreen having branches to which the needles are attached and from which the needles extend. The branch material (preferably fresh) is irradiated with gamma radiation at an energy level of 0.5 to 2.5 MRAD or higher, effective to loosen the attachment of the needles to the branch material. Then, the needles are recovered, by collecting those that fall off during or after the irradiation, plus agitating the branch material or touching the needles by hand or with suitable apparatus. The needles are easily detached from the branch material and are then collected.

This invention is thus applicable to a large variety of needle-bearing species including balsam, larch, pine (such as white, red, loblolly, scotch, and the like), fir (such as Douglas fir), spruce, hemlock, bald cypress and sequoia.

The invention is also notable in that plant material, fresh or dehydrated, that has been irradiated as taught herein exhibits little or no tendency to heat up and/or undergo fermenting and/or composting when it is packed together.

The invention will be described further with reference to the following examples, which are intended for purposes of illustration and should not be construed as limiting the scope of this invention.

EXAMPLE 1

As a simple illustration of the application of this invention, 63 kg of fresh branches *Abias balsamea* L. were gamma irradiated (1.5 to 2.5 MRAD). 37.2 kg of needles were easily recovered. Many had simply fallen off the branches, the rest fell with simple shaking of the branches. There remained 22.6 kg of branches (approximately 3 kg of water was lost during gamma irradiation). The fresh needles were exhaustively extracted in an extraction unit illustrated in the figure and described herein. 12 gallons of 1,1,1-trichloroethane were used. The yield of resin was found to be 3.2% and the maltol content was 12.5%.

EXAMPLE 2

This example shows that dehydration of gamma irradiated fir needles has little effect on the maltol content. On the contrary, dehydration of untreated needles results in a substantial reduction of recoverable maltol content.

Fresh *Abias balsamea* L. needles (46% humidity) were extracted with 1,1,1-trichloroethane yielding 2.3% resin with 19.5% maltol in it.

Needles dehydrated at 40° C. for two days to a 12% residual humidity yielded (upon extracting using the same conditions) 4% resin with maltol content of 4.6%.

On the contrary, extraction of dehydrated needles (using the same extraction conditions) which prior to dehydration were treated by gamma irradiation at 2.3-3.1 MRAD, yielded 4% resin with 20% maltol in it.

EXAMPLE 3

This experiment shows that gamma irradiation caused a substantial increase in the content of recoverable maltol.

A shipment of branches of *Abias balsamea* L. was found to be of rather poor quality in terms of maltol content. The yield of resin was about 1.8% and the maltol content in the resin was approximately 3%. The same material after irradiation (at 2.3-3.1 MRAD) showed essentially the same yield of resin but the maltol content was on the average of 18%.

EXAMPLE 4

Since dehydration of gamma irradiated needles has little if any effect on the maltol content it becomes feasible to use water-soluble non-chlorinated polar solvents as an extracting agent.

500 grams of irradiated and dehydrated fir needles were extracted by boiling in 1.5 liters of methanol. The yield of resin was found to be 25% and the maltol content in the resin 8.3%. It must be recognized that although the term "resin" is used for the methanol extract and for the extract with chlorinated solvents, these two resins are very different in overall chemical composition, since different solvents extract different constituents from the plant material. However, the effectiveness in permitting maltol recovery even with a polar solvent, is clear.

EXAMPLE 5

A batch of fresh branches (*Abias balsamea* L.) was collected in Eastern Quebec, Canada. Fresh needles were separated by hand from a representative sample of this batch and analyzed for moisture content, resin content and maltol content. The moisture content was found to be 54%. The resin content and the maltol content were found to be 7.8% and 1.26%, respectively. Calculations were based upon absolutely dry weight basis.

One kilogram of fresh needles was air dried at about 30° C. for three weeks to a residual moisture content of 3.5%. The yield of the resin from air dried needles was found to be 6.5% while the maltol content was 0.4%. This confirms previously established findings that drying of the needles results in a 3-4 fold decrease in the maltol content.

Fresh fir branches were treated by gamma irradiation at three levels:

A. 0.7 to 0.9 MRAD
B. 1.7 to 1.9 MRAD
C. 2.6 to 3.0 MRAD

It was reconfirmed that gamma irradiation at all three of the tested levels causes substantial weakening of the bond between the needles and the branch. The needles easily and quantitatively fell off the branches upon simple mechanical shaking. The percentage of fresh needles was found to be approximately 54% of the mass, whereas 46% of the mass was woody parts. The content of the resin and the percentage of maltol in it was determined separately in each of the three gamma irradiated samples. The resin content in gamma irradiated needles was found to be nearly identical to that of the fresh untreated needles. The maltol content, however was found to be 1.53% for sample A, 1.55% for sample B and 1.60% for sample C (calculated on absolutely dry weight basis).

This confirms that gamma irradiation of the fresh foliage of the fir tree results in a noticeable increase of the maltol content recovered in the product fraction.

Figure 2:
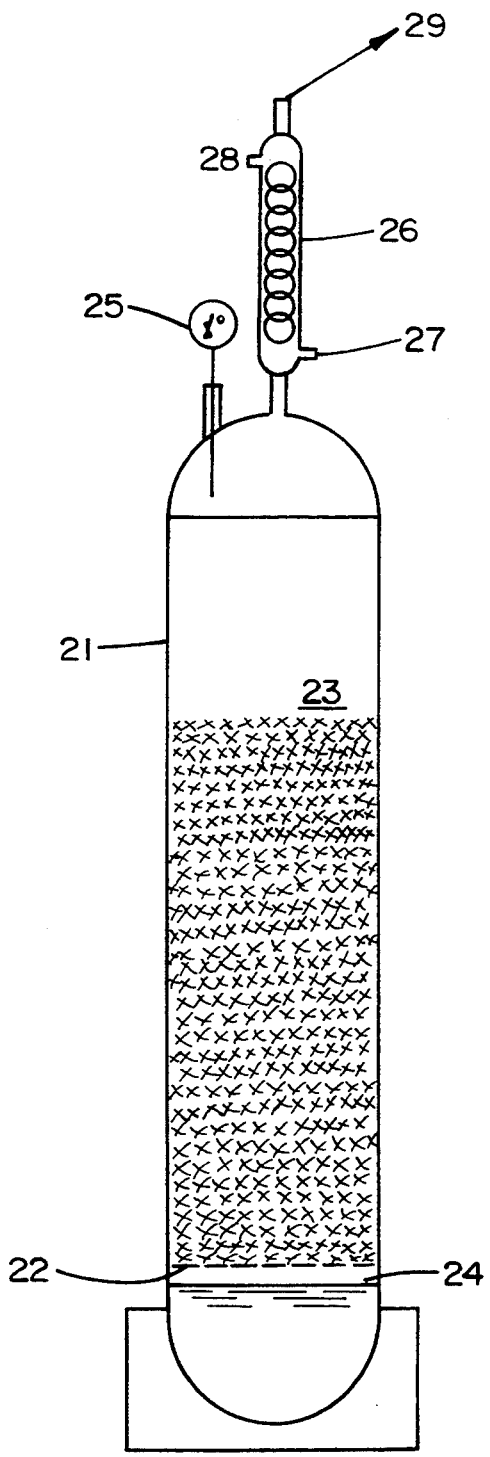
FIG. 2 is a cross-sectional view of another apparatus preferred for use in recovering aromatic principle from material obtained through use of the present invention.

FIG. 2 depicts an apparatus useful in extracting maltol from irradiated needles into water. Column 21 is equipped with a porous bottom plate 22 on which rests a charge 23 of needles. Water for extraction is fed into column 21 at point 24. A heater and a stirrer (not shown) are maintained at the bottom of column 21. Column 21 is also fitted with a temperature gauge 25 and a reflux condenser 26 to which condensing water is fed at point 27 and from which the condensing water is withdrawn at point 28. A vacuum is drawn via exit port 29 to maintain a vacuum over the charge 23.

To illustrate the apparatus of FIG. 2 and to confirm the effectiveness of the present invention, 1.5 kilograms of fresh irradiated needles was subjected to liquid-vapor extraction in water in the apparatus presented in FIG. 2. The extraction was conducted under slightly reduced pressure to maintain the process temperature at 60° C. Three liters of water was introduced into the apparatus at the beginning of the process which lasted for about four hours. At the end of the process, spent plant material was removed from the apparatus and analyzed for residual maltol content. This was found to be 0.25% which corresponds to 84% of the maltol recovery.

Water was stripped from the aqueous extract (in which the maltol content was found to be about 2%) by evaporation under vacuum. Substantially pure maltol was recovered from very viscous dark brown residue in the following two ways:

1. Co-distillation with alpha pinene as described in U.S. Pat. No. 5,221,756.
2. Dissolving of the residue in hot methanol, cooling and filtration of the resulting insoluble precipitate, and crystallization of maltol from partially concentrated filtrate.

What is claimed is:

1. A process for recovering maltol from source material containing maltol, comprising:
   (a) irradiating said source material with gamma irradiation; and
   (b) extracting maltol from said irradiated source material.

2. A process according to claim 1 wherein said maltol is extracted from said irradiated source material by extracting said maltol from said source material into water.

3. A process according to claim 1 wherein said maltol is extracted from said irradiated source material by extracting said maltol from said source material into a liquid solvent.

4. A process according to claim 1 wherein said maltol is extracted from said irradiated source material by extracting said maltol from said source material into a solution of a polar solvent and water.

5. A process according to claim 1 wherein said maltol is extracted from said irradiated source material by extracting said maltol from said source material into a water-immiscible solvent.

6. A process according to claim 1 wherein said source material is plant material.

7. A process according to claim 6 wherein said maltol is extracted from said irradiated source material by extracting said maltol from said source material into water.

8. A process according to claim 6 wherein said maltol is extracted from said irradiated source material by extracting said maltol from said source material into a liquid solvent.

9. A process according to claim 6 wherein said maltol is extracted from said irradiated source material by extracting said maltol from said source material into a solution of a liquid solvent and water.

10. A process according to claim 6 wherein said maltol is extracted from said irradiated source material by extracting said maltol from said source material into a water-immiscible solvent.

11. The process according to claim 1 wherein the irradiated source material is dehydrated prior to maltol extraction.

12. In the recovery of maltol from source material containing maltol, wherein said source material is treated to extract therefrom a product fraction comprising maltol, the improvement comprising, prior to extracting maltol from said source material, irradiating said source material with gamma radiation effective to increase the yield of maltol in said extraction.

13. The process according to claim 12 wherein the irradiated source material is dehydrated prior to maltol extraction.

14. A process for recovering maltol from plant material which comprises branch material and needles extending from said branch material comprising
   (a) irradiating said branches and needles with gamma radiation under conditions effective to loosen the attachment of said needles to said branches;
   (b) recovering said needles separate from said branches; and
   (c) recovering maltol from said needles.

15. A process for recovering needles from branch material having needles attached thereto and extending therefrom, comprising irradiating said branch material with gamma radiation at a level effective to lessen the attachment of said needles to said branch material, and thereafter collecting said needles separate from said branch material.

16. A process according to claim 15 wherein said branch material is from one or more plants selected from the group consisting of balsam, larch, pine, spruce, fir, hemlock, bald cypress and Sequoia.

* * * * *